(12) United States Patent
Taugerbeck et al.

(10) Patent No.: US 7,425,356 B2
(45) Date of Patent: *Sep. 16, 2008

(54) CHIRAL COMPOUNDS

(75) Inventors: Andreas Taugerbeck, Darmstadt (DE);
Peer Kirsch, Seeheim-Jugenheim (DE);
Detlef Pauluth, Ober-Ramstadt (DE);
Joachim Krause, Dieburg (DE); Juliane Suermann, Darmstadt (DE); Michael Heckmeier, Hemsbach (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 11/753,400

(22) Filed: May 24, 2007

(65) Prior Publication Data

US 2007/0229732 A1      Oct. 4, 2007

Related U.S. Application Data

(62) Division of application No. 10/477,896, filed on Nov. 19, 2003, now Pat. No. 7,223,450.

(30) Foreign Application Priority Data

May 21, 2001    (EP)    .................. 01111954

(51) Int. Cl.
*C09K 19/52* (2006.01)
*C09K 19/38* (2006.01)
*C09K 19/58* (2006.01)
*C09K 19/54* (2006.01)
*C07D 321/00* (2006.01)
*C07D 323/00* (2006.01)

(52) U.S. Cl. ............ 428/1.1; 252/299.01; 549/348

(58) Field of Classification Search ............ 252/299.01, 252/299.5, 299.1, 299.2; 428/1.1, 1.3, 1.31; 549/348, 358, 382; 349/106
See application file for complete search history.

(56) References Cited

U.S. PATENT DOCUMENTS

| | | | |
|---|---|---|---|
| 7,223,450 B2 * | 5/2007 | Taugerbeck et al. | .......... 428/1.1 |
| 2004/0089843 A1 | 5/2004 | Suermann et al. | |
| 2004/0155221 A1 | 8/2004 | Hammond-Smith et al. | |
| 2004/0173775 A1 | 9/2004 | Suermann et al. | |
| 2005/0219447 A1 | 10/2005 | Staney et al. | |

OTHER PUBLICATIONS

Green M.M. et al.: "Mechanism of the transformation of a stiff polymer lyotropic nematic liquid crystal to the cholesteric state by dopant-mediated chiral information transfer" Journal of the American Chemical Society., vol. 120, No. 38, Sep. 30, 1998, 9810-9817, XP002214617.
Gottarelli G. et al. "Induction of the cholesteric mesophase in nematic liquid crystals: mechanism and application to the determination of bridged biaryl configurations" Journal of the American Chemical Society., vol. 105, No. 25, Dec. 14, 1983, pp. 7318-7321, XP002214618.
Kuball H-G et al. "Chirality and circular dichroism of oriented molecules and anisotropic phases" Chirality, Wiley-Liss, New York, US, vol. 12, No. 4, 2000, pp. 278-286, XP001041318.
Zhang M. et al. "Chirochromism-photo-chromism by epimerization: search for a liquid crystal phototrigger" Journal of the American Chemical Society, American Chemical Society, Washington, DC, US, vol. 116, No. 11, Jun. 1, 1994, pp. 4852-4857, XP002189468.
Kelly S M et al. Four-unit linking groups v. optically active dopants: Liquid crystals, Taylor and Francis Ltd, London, GB, vol. 11, No. 5, 1992, pp. 761-771, XP000606158.
CAPLUS: 1991:42238.
CAPLUS: 1994: 495658.
CAPLUS: 1996: 45831.

* cited by examiner

*Primary Examiner*—Shean C Wu
(74) *Attorney, Agent, or Firm*—Miller, White, Zelano, Branigan, P.C.

(57) ABSTRACT

The invention relates to chiral compounds of formula I wherein $X^1, X^2, X^1, X^2, x^1, x^2, y^1, y^2, B, C, U^1, U^2, V^1, V^2, W^1$ and $W^2$ have the meaning given in claim 1, to liquid crystal mixtures comprising at least one chiral compound of formula I, to chiral linear or crosslinked liquid crystal polymers obtainable by polymerizing a polymerizable mixture comprising at least one chiral compound of formula I, to the use of chiral compound of formula I and mixtures and polymers obtained thereof in liquid crystal displays, active and passive optical elements, adhesives, synthetic resins with anisotropic mechanical properties, cosmetic and pharmaceutical compositions, diagnostics, liquid crystal pigments, for decorative and security applications, nonlinear optics, optical information storage or as chiral dopants, and to a liquid crystal display comprising a mixture comprising at least one chiral compound of formula I.

24 Claims, No Drawings

CHIRAL COMPOUNDS

This application is a divisional of U.S. Ser. No. 10/477,896, filed Nov. 19, 2003, now U.S. Pat. No. 7,223,450; U.S. Ser. No. 10/477,896 is a 371 National Stage application of International Application No. PCT/EP02/04574 filed Apr. 25, 2002.

The invention relates to chiral compounds, to liquid crystal mixtures containing the chiral compounds, to polymers obtained from the chiral compounds and liquid crystal mixtures, and to the use of the chiral compounds, liquid crystal mixtures and polymers obtained thereof in liquid crystal displays, active and passive optical elements like polarizers, compensators, alignment layers, colour filters or holographic elements, in adhesives, synthetic resins with anisotropic mechanical properties, cosmetic and pharmaceutical compositions, diagnostics, liquid crystal pigments, for decorative and security applications, in nonlinear optics, optical information storage or as chiral dopants.

Chiral compounds can be used as dopants to induce or enhance a helical twist in a liquid crystal mixture that is used for example in liquid crystal displays. The pitch p of the molecular helix in the first approximation, which is sufficient for most practical applications, is inversely proportional to the concentration c of the chiral dopant in the liquid crystal host mixture according to equation (1):

$$p = \frac{1}{HTP} \cdot \frac{1}{c} \qquad (1)$$

The proportionality factor is the helical twisting power (HTP) of the chiral dopant.

For many applications it is desirable to have LC mixtures with a twisted phase. Among these are e.g. phase-change displays, guest-host displays, passive and active matrix TN and STN displays like AMD-TN, ferroelectric displays and cholesteric displays like SSCT (surface stabilized cholesteric texture) or PSCT (polymer stabilized cholesteric texture) displays, including displays with temperature compensated characteristics, e.g. by appropriate selection of the cholesteric compounds according to the invention either alone or in combination with further chiral dopants. For these applications it is advantageous to have available a chiral dopant with a high HTP in order to reduce the amount of dopant needed to induce the desired pitch.

For some applications it is desired to have LC mixtures that exhibit a strong helical twist and thereby a short pitch length. For example in liquid crystal mixtures that are used in selectively reflecting cholesteric displays like SSCT or PSCT, the pitch has to be selected such that the maximum of the wavelength reflected by the cholesteric helix is in the range of visible light. Another possible application are polymer films with a chiral liquid crystal phase for optical elements, such as cholesteric broadband polarizers or retardation films.

As can be seen from equation (1), a short pitch can be achieved by using high amounts of dopant or by using a dopant with a high HTP.

Chiral compounds are disclosed for example in WO 95/16007, WO 98/00428 and GB 2 328 207 A.

However, the chiral dopants of prior art often exhibit low values of the HTP, so that high amounts of dopant are needed. This is a disadvantage because chiral dopants can be used only as pure enantiomers and are therefore expensive and difficult to synthesize.

Furthermore, when using chiral dopants of prior art in high amounts, they often negatively affect the properties of the liquid crystal host mixture, such as e.g. the clearing point, the dielectric anisotropy $\Delta\in$, the viscosity, the driving voltage or the switching times.

Another disadvantage of prior art chiral compounds is that they often show low solubility in the liquid crystal host mixture, which leads to undesired crystallization at low temperatures. To overcome this disadvantage, typically two or more different chiral dopants have to be added to the host mixture. This implies higher costs and also requires additional effort for temperature compensation of the mixture, as the different dopants have to be selected such that their temperature coefficients of the twist compensate each other.

Consequently, there is a considerable demand for chiral compounds with a high HTP which are easy to synthesize, can be used in low amounts, show improved temperature stability of the cholesteric pitch e.g. for utilizing a constant reflection wavelength, do not affect the properties of the liquid crystal host mixture and show good solubility in the host mixture.

The invention has the aim of providing chiral compounds having these properties, but which do not have the disadvantages of the chiral dopants of the state of the art as discussed above.

Another aim of the invention is to extend the pool of chiral compounds that can be used as dopants available to the expert.

It has been found that these aims can be achieved by providing chiral compounds as described below.

Thus, one object of the present invention are chiral compounds of formula I

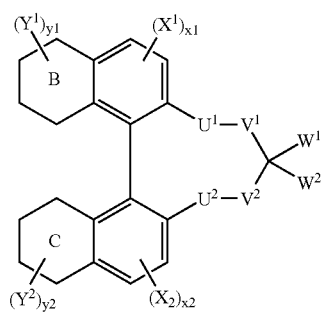

I wherein $X^1, X^2, Y^1$ and $Y^2$ are independently of each other F, Cl, Br, I, CN, SCN, $SF_5$, straight chain or branched alkyl with up to 25 C atoms which may be unsubstituted, mono- or polysubstituted by F, Cl, Br, I or CN, it being also possible for one or more non-adjacent $CH_2$ groups to be replaced, in each case independently from one another, by —O—, —S—, —NH—, —NR⁰—, —CO—, —COO—, —OCO—, —OCO—O—, —S—CO—, —CO—S—, —CH=CH— or —C≡C— in such a manner that O and/or S atoms are not linked directly to one another, a polymerizable group, or cycloalkyl or aryl with up to 20 C atoms that is optionally mono- or polysubstituted by L or by a polymerizable group, $R^0$ is H or alkyl with 1 to 4 C atoms, $x^1$ and $x^2$ are independently of each other 0, 1 or 2, $y^1$ and $y^2$ are independently of each other 0, 1, 2, 3 or 4, B and C are independently of each other an aromatic or partially or fully saturated aliphatic six-membered ring, wherein one or more CH groups may be replaced by N and one or more $CH_2$ groups may be replaced by O and/or S, one of $W^1$ and $W^2$ is $-Z^1-A^1-(Z^2-A^2)_m-R$ and the other is $R^1$ or $A^3$, or both of $W^1$ and $W^2$ are $-Z^1 A^1-(Z^2-A^2)_m-R$, with $W^1$ and $W^2$ not being at the same time H, or

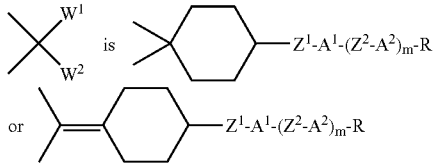

$U^1$ and $U^2$ are independently of each other $CH_2$, O, S, CO or CS, $V^1$ and $V^2$ are independently of each other $(CH_2)_n$, wherein up to four non-adjacent $CH_2$-groups may be replaced by O and/or S, and one of $V^1$ and $V^2$, or, in case

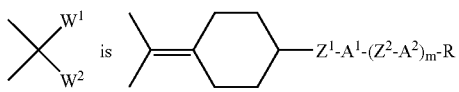

one or both of $V^1$ and $V^2$ may also denote a single bond, n is an integer from 1 to 7, $Z^1$ and $Z^2$ are independently of each other —O—, —S—, —CO—, —COO—, —OCO—, —O—COO—, —CO—$NR^0$—, —$NR^0$—CO—, —$OCH_2$—, —$CH_2O$—, —$SCH_2$—, —$CH_2S$—, —$CF_2O$—, —$OCF_2$—, —$CF_2S$—, —$SCF_2$—, —$CH_2CH_2$—, —$CF_2CH_2$—, —$CH_2CF_2$—, —$CF_2CF_2$—, —CH=N—, —N=CH—, —N=N—, —CH=CH—, —CF=CH—, —CH=CF—, —CF=CF—, —C≡C—, —CH=CH—COO—, —OCO—CH=CH— or a single bond, $A^1$, $A^2$ and $A^3$ are independently of each other 1,4-phenylene in which, in addition, one or more CH groups may be replaced by N, 1,4-cyclohexylene in which, in addition, one or two non-adjacent $CH_2$ groups may be replaced by O and/or S, 1,3-dioxolane-4,5-diyl, 1,4-cyclohexenylene, 1,4-bicyclo-(2,2,2)-octylene, piperidine-1,4-diyl, naphthalene-2,6-diyl, decahydronaphthalene-2,6-diyl, or 1,2,3,4-tetrahydronaphthalene-2,6-diyl, it being possible for all these groups to be unsubstituted, mono- or polysubstituted with L, and $A^1$ may also be a single bond, L is halogen or a cyano, nitro, alkyl, alkoxy, alkylcarbonyl or alkoxycarbonyl group with 1 to 7 C atoms, wherein one or more H atoms may be substituted by F or Cl, m is in each case independently 0, 1, 2 or 3, and R and $R^1$ are independently of each other H, F, Cl, Br, I, CN, SCN, OH, $SF_5$, straight chain or branched alkyl with up to 25 C atoms which may be unsubstituted, mono- or polysubstituted by F, Cl, Br, I or CN, it being also possible for one or more non-adjacent $CH_2$ groups to be replaced, in each case independently from one another, by —O—, —S—, —NH—, —$NR^0$—, —CO—, —COO—, —OCO—, —OCO—O—, —S—CO—, —CO—S—, —CH=CH— or —C≡C— in such a manner that O and/or S atoms are not linked directly to one another, or a polymerizable group.

Another object of the invention is a liquid crystal mixture containing at least one compound of formula I.

Another object of the present invention is a polymerizable liquid crystal mixture comprising at least one compound of formula I.

Another object of the invention is a linear or crosslinked anisotropic polymer with twisted structure obtainable from a polymerizable liquid crystal mixture comprising one or more compounds of formula I.

A further object of the invention is the use of compounds of formula I or a liquid crystal mixture or anisotropic polymer film comprising them in liquid crystal displays, such as STN, TN, AMD-TN, temperature compensation, ferroelectric, guest-host, phase change or surface stabilized or polymer stabilized cholesteric texture (SSCT, PSCT) displays, in active and passive optical elements like polarizers, compensators, alignment layers, colour filters or holographic elements, in adhesives, synthetic resins with anisotropic mechanical properties, cosmetic and pharmaceutical compositions, diagnostics, liquid crystal pigments, for decorative and security applications, in nonlinear optics, optical information storage or as chiral dopants.

Yet another object of the invention is a liquid crystal display comprising a liquid crystal mixture comprising at least one chiral compound of formula I.

The inventive chiral compounds bear several advantages
they exhibit a high HTP,
they exhibit a good solubility in liquid crystal mixtures,
they exhibit broad liquid crystalline phases,
when inventive compounds are used as chiral dopant in a liquid crystal mixture, due to their high solubility higher amounts of dopant can be used to produce a high twist (=a low pitch),
in case high amounts of dopants are needed, due to the broad liquid crystalline phases of the inventive dopants the liquid crystal phase of the host mixture is less negatively influenced,
due to their high HTP, lower amounts of inventive dopants are needed to achieve a high pitch, and thereby the liquid crystalline properties of the mixture are less negatively affected,
enantiomerically pure inventive chiral compounds are easy to prepare,
the availability of both helices is a considerable advantage, e.g. for the use in security applications, as it enables the production of chiral films or coatings reflecting circularly polarized light of a single handedness.

The inventive chiral compounds are mesogenic or even liquid crystalline, i.e. they can induce or enhance mesophase behaviour for example in admixture with other compounds, or even exhibit one or more mesophases themselves. It is also possible that the inventive compounds show mesophase behaviour only in mixtures with other compounds, or, in case of polymerizable compounds, when being (co)polymerized. Mesogenic inventive chiral compounds are especially preferred.

Especially preferred are the following compounds of formula I at least one of B and C, preferably both B and C are aromatic rings.

at least one of B and C, preferably both B and C contain two saturated C atoms.

at least one of B and C, preferably both B and C contain four saturated C atoms.

at least one of $U^1$ and $U^2$, very preferably both $U^1$ and $U^2$ are 0.

$V^1$ and $V^2$ are $(CH_2)_n$, wherein n is 1, 2, 3 or 4, very preferably one of $V^1$ and $V^2$ is $CH_2$ and the other is $CH_2$ or $(CH_2)_2$.

one of $V^1$ and $V^2$ is $CH_2$ and the other is a single bond.

at least one of $Z^1$ and $Z^2$ is —$CF_2O$—, —$OCF_2$— or —$CF_2CF_2$—. These compounds have a particular high solubility in liquid crystal mixtures.

$Z^1$ is a single bond.

at least one of the groups $Z^1$ and $Z^2$ is —$CF_2O$—, —$OCF_2$—, —$CF_2CF_2$— or —$CF$=$CF$— and the other are —$COO$—, —$OCO$—, —$CH_2$—$CH_2$— or a single bond.

at least one of $Z^1$ and $Z^2$ is —C≡C—. These compounds are especially suitable for uses where highly birefringent materials are needed.

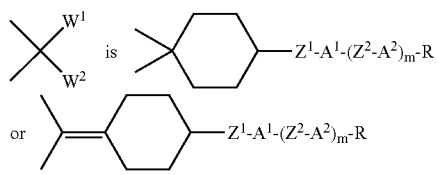

and m is 0 or 1, in particular 0, very preferably m is 0 and $A^1$ is a single bond.

$W^1$ is $R^1$ or $A^3$, in particular H or F, and $W^2$ is -$Z^1$-$A^1$-($Z^2$-$A^2$)$_m$-R with m being 1 or 2.

$x^1$ and $x^2$ are 1.

$Y^1$ and $y^2$ are 1.

$x^1$, $x^2$, $y^1$ and $y^2$ are 0.

at least one, preferably one or two of $X^1$, $X^2$, $Y^1$ and $Y^2$ denote or comprise a polymerizable group.

R is a polymerizable group.

R is straight chain alkyl with 1 to 12 C atoms wherein one or more H atoms may be replaced with F or CN, it being also possible for one or more non-adjacent $CH_2$ groups to be replaced, in each case independently from one another, by —O—, —S—, —NH—, —N($CH_3$)—, —CO—, —COO—, —OCO—, —OCO—O—, —S—CO—, —CO—S—, —CH=CH— or —C≡C— in such a manner that oxygen atoms are not linked directly to one another, very preferably alkyl or alkoxy with 1 to 12 C atoms.

R is $(CH_2)_f$—OH, with f being 0 or an integer from 1 to 12.

$X^1$, $X^2$, $Y^1$, $Y^2$ and $R^1$ are selected from H, F and straight chain alkyl with 1 to 12 C atoms wherein one or more H atoms may be replaced with F or CN, it being also possible for one or more non-adjacent $CH_2$ groups to be replaced, in each case independently from one another, by —O—, —S—, —NH—, —N($CH_3$)—, —CO—, —COO—, —OCO—, —OCO—O—, —S—CO—, —CO—S—, —CH=CH— or —C≡C— in such a manner that oxygen atoms are not linked directly to one another, and are very preferably H, F and alkyl or alkoxy with 1 to 12 C atoms.

$X^1$, $X^2$, $Y^1$ and $Y^2$ are aryl, preferably phenyl, that is unsubstituted or mono- or polysubstituted, preferably monosubstituted in 4-position, with L.

L is F, Cl, CN or optionally fluorinated alkyl, alkoxy, alkylcarbonyl or alkoxycarbonyl with 1 to 7 C-atoms.

L is F, Cl, CN, $NO_2$, $CH_3$, $C_2H_5$, $OCH_3$, $OC_2H_5$, $COCH_3$, $COC_2H_5$, $CF_3$, $CHF_2$, $CH_2F$, $OCF_3$ $OCHF_2$, $OCH_2F$ or $OC_2F_5$.

$A^3$ is 1,4-phenylene or 1,4-cyclohexylene that is optionally substituted with up 5, very preferably 1, 2 or 3 F or Cl atoms or CN, $NO_2$, alkyl, alkoxy, alkylcarbonyl or alkoxycarbonyl groups with 1 to 4 C atoms wherein one or more H atoms may be substituted by F or Cl.

$A^1$ and $A^2$ are selected from 1,4-phenylene and trans-1,4-cyclohexylene that are unsubstituted or substituted with up to 4 groups L.

the mesogenic group -$Z^1$-$A^1$-($Z^2$-$A^2$)$_m$ incorporates one, two or three five- or six-membered rings.

the mesogenic group -$Z^1$-$A^1$-($Z^2$-$A^2$)$_m$ is bicyclohexyl, biphenyl, phenylcyclohexyl, cyclohexylphenyl or biphenylcyclohexyl, wherein the phenyl rings are optionally substituted with one or two F atoms.

A smaller group of preferred mesogenic groups -$Z^1$-$A^1$-($Z^2$-$A^2$)$_m$ is listed below. For reasons of simplicity, Phe in these groups is 1,4-phenylene which may also substituted by one or more groups L as defined above, Cyc is 1,4-cyclohexylene and Z has in each case independently one of the meanings of $Z^1$ in formula I. The list of preferred mesogenic groups is comprising the following formulae as well as their mirror images

| | |
|---|---|
| -Phe- | II-1 |
| -Cyc- | II-2 |
| -Phe-Z-Phe- | II-3 |
| -Phe-Z-Cyc- | II-4 |
| -Cyc-Z-Cyc- | II-5 |
| -Phe-Z-Phe-Z-Phe- | II-6 |
| -Phe-Z-Phe-Z-Cyc- | II-7 |
| -Phe-Z-Cyc-Z-Phe- | II-8 |
| -Cyc-Z-Phe-Z-Cyc- | II-9 |
| -Cyc-Z-Cyc-Z-Phe- | II-10 |
| -Cyc-Z-Cyc-Z-Cyc- | II-11 |

Particularly preferred are the subformulae II-3, II-4, II-5, II-6, II-7 and II-10, in particular II-4 and II-5.

Further preferred are subformula II-5, wherein Z is —$CF_2CF_2$— and subformula II-3 and II-4, wherein Z is —$OCF_2$—.

Further preferred are subformulae II-10 and II-11, wherein one or both of Z between two cyclohexylene rings are —$CF_2CF_2$—, and subformulae II-6, II-7, II-8, II-9, and II-10, wherein one or both of Z between two phenylene rings or between a phenylene and a cyclohexylene ring are —$OCF_2$— or —$CF_2O$—, with the O atom being adjacent to the phenylene ring.

The other groups Z are preferably —COO—, —OCO—, —$CH_2CH_2$— or a single bond.

Further preferred are compounds wherein the mesogenic group comprises at least one group Phe that is substituted with one or two groups L, preferably in 3- and/or 5-position, further preferably in 2- and/or 3-position, and L is F, Cl, $CH_3$, $OCH_3$, $CF_3$, $CHF_2$, $CH_2F$, $OCF_3$ $OCHF_2$, $OCH_2F$ or CN.

L is preferably F, Cl, CN, $NO_2$, $CH_3$, $C_2H_5$, $OCH_3$, $OC_2H_5$, $COCH_3$, $COC_2H_5$, $CF_3$, $CHF_2$, $CH_2F$, $OCF_3$ $OCHF_2$, $OCH_2F$, $OC_2F_5$, in particular F, Cl, CN, $CH_3$, $CHF_2$, $C_2H_5$, $OCH_3$, $OCHF_2$, $CF_3$ and $OCF_3$, most preferably F, $CH_3$, $CF_3$, $OCH_3$, $OCHF_2$ and $OCF_3$.

If $X^1$, $X^2$, $Y^1$, $Y^2$, R or $R^1$ in formula I is an alkyl or alkoxy radical, i.e. where the terminal $CH_2$ group is replaced by —O—, this may be straight-chain or branched. It is preferably straight-chain, has 2, 3, 4, 5, 6, 7 or 8 carbon atoms and accordingly is preferably ethyl, propyl, butyl, pentyl, hexyl, heptyl, octyl, ethoxy, propoxy, butoxy, pentoxy, hexoxy, heptoxy, or octoxy, furthermore methyl, nonyl, decyl, undecyl, dodecyl, tridecyl, tetradecyl, pentadecyl, nonoxy, decoxy, undecoxy, dodecoxy, tridecoxy or tetradecoxy, for example.

Oxaalkyl, i.e. where one $CH_2$ group is replaced by —O—, is preferably straight-chain 2-oxapropyl (=methoxymethyl), 2- (=ethoxymethyl) or 3-oxabutyl (=2-methoxyethyl), 2-, 3-, or 4-oxapentyl, 2-, 3-, 4-, or 5-oxahexyl, 2-, 3-, 4-, 5-, or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-, 6-, 7-, 8- or 9-oxadecyl, for example.

Halogen is preferably F or Cl.

$X^1$, $X^2$, $Y^1$, $Y^2$, R or $R^1$ in formula I can be a polar or an unpolar group. In case of a polar group, it is selected from CN, OH, $SF_5$, halogen, $OCH_3$, SCN, $COR^5$, $COOR^5$ or a mono-oligo- or polyfluorinated alkyl or alkoxy group with 1 to 4 C atoms. $R^5$ is optionally fluorinated alkyl with 1 to 4, preferably 1 to 3 C atoms. Especially preferred polar groups are selected of F, Cl, CN, $OCH_3$, $COCH_3$, $COC_2H_5$, $COOCH_3$, $COOC_2H_5$, $CF_3$, $CHF_2$, $CH_2F$, $OCF_3$, $OCHF_2$, $OCH_2F$, $C_2F_5$ and $OC_2F_5$, in particular F, Cl, CN, $CF_3$, $OCHF_2$ and $OCF_3$. In case of an unpolar group, it is preferably alkyl with up to 15 C atoms or alkoxy with 2 to 15 C atoms.

$X^1$, $X^2$, $Y^1$, $Y^2$, R or $R^1$ in formula I can be an achiral or a chiral group. In case of a chiral group it is preferably selected of formula III:

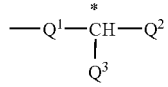

III wherein $Q^1$ is an alkylene or alkylene-oxy group with 1 to 9 C atoms or a single bond, $Q^2$ is an alkyl or alkoxy group with 1 to 10 C atoms which may be unsubstituted, mono- or polysubstituted by F, Cl, Br or CN, it being also possible for one or more non-adjacent $CH_2$ groups to be replaced, in each case independently from one another, by —C≡C—, —O—, —S—, —NH—, —N($CH_3$)—, —CO—, —COO—, —OCO—, —OCO—O—, —S—CO— or —CO—S— in such a manner that oxygen atoms are not linked directly to one another, $Q^3$ is F, Cl, Br, CN or an alkyl or alkoxy group as defined for $Q^2$ but being different from $Q^2$.

In case $Q^1$ in formula III is an alkylene-oxy group, the O atom is preferably adjacent to the chiral C atom.

Preferred chiral groups of formula III are 2-alkyl, 2-alkoxy, 2-methylalkyl, 2-methylalkoxy, 2-fluoroalkyl, 2-fluoroalkoxy, 2-(2-ethin)-alkyl, 2-(2-ethin)-alkoxy, 1,1,1-trifluoro-2-alkyl and 1,1,1-trifluoro-2-alkoxy.

Particularly preferred chiral groups are 2-butyl (=1-methylpropyl), 2-methylbutyl, 2-methylpentyl, 3-methylpentyl, 2-ethylhexyl, 2-propylpentyl, in particular 2-methylbutyl, 2-methylbutoxy, 2-methylpentoxy, 3-methylpentoxy, 2-ethylhexoxy, 1-methylhexoxy, 2-octyloxy, 2-oxa-3-methylbutyl, 3-oxa-4-methylpentyl, 4-methylhexyl, 2-hexyl, 2-octyl, 2-nonyl, 2-decyl, 2-dodecyl, 6-methoxyoctoxy, 6-methyloctoxy, 6-methyloctanoyloxy, 5-methylheptyloxycarbonyl, 2-methylbutyryloxy, 3-methylvaleroyloxy, 4-methylhexanoyloxy, 2-chlorpropionyloxy, 2-chloro-3-methylbutyryloxy, 2-chloro-4-methylvaleryloxy, 2-chloro-3-methylvaleryloxy, 2-methyl-3-oxapentyl, 2-methyl-3-oxahexyl, 1-methoxypropyl-2-oxy, 1-ethoxypropyl-2-oxy, 1-propoxypropyl-2-oxy, 1-butoxypropyl-2-oxy, 2-fluorooctyloxy, 2-fluorodecyloxy, 1,1,1-trifluoro-2-octyloxy, 1,1,1-trifluoro-2-octyl, 2-fluoromethyloctyloxy for example. Very preferred are 2-hexyl, 2-octyl, 2-octyloxy, 1,1,1-trifluoro-2-hexyl, 1,1,1-trifluoro-2-octyl and 1,1,1-trifluoro-2-octyloxy.

In addition, compounds of formula I containing an achiral branched group $X^1$, $X^2$, $Y^1$, $Y^2$, R or $R^1$ may occasionally be of importance, for example, due to a reduction in the tendency towards crystallization. Branched groups of this type generally do not contain more than one chain branch. Preferred achiral branched groups are isopropyl, isobutyl (=methylpropyl), isopentyl (=3-methylbutyl), isopropoxy, 2-methyl-propoxy and 3-methylbutoxy.

In case of compounds comprising a polymerizable group, this is preferably selected of the formula P-Sp-X, wherein P is $CH_2=CW^1$—COO—,

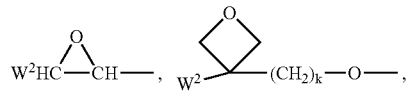

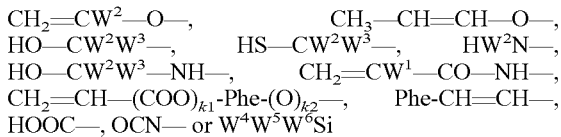

$CH_2=CW^2$—O—, $CH_3$—CH=CH—O—, HO—$CW^2W^3$—, HS—$CW^2W^3$—, $HW^2N$—, HO—$CW^2W^3$—NH—, $CH_2=CW^1$—CO—NH—, $CH_2$=CH—(COO)$_{k1}$-Phe-(O)$_{k2}$—, Phe-CH=CH—, HOOC—, OCN— or $W^4W^5W^6Si$

Sp is a spacer group having 1 to 25 C atoms or a single bond,

X is —O—, —S—, —$OCH_2$—, —$CH_2O$—, —CO—, —COO—, —OCO—, —OCO—O—, —CO—$NR^0$—, —$NR^0$—CO—, —$OCH_2$—, —$CH_2O$—, —$SCH_2$—, —$CH_2S$—, —CH=CH—COO—, —OOC—CH=CH— or a single bond, $W^1$ is H, Cl, CN, phenyl or alkyl with 1 to 5 C-atoms, in particular H, $C_1$ or $CH_3$, $W^2$ and $W^3$ are independently of each other H or alkyl with 1 to 5 C-atoms, in particular methyl, ethyl or n-propyl, $W^4$, $W^5$ and $W^6$ are independently of each other Cl, oxaalkyl or oxacarbonylalkyl with 1 to 5 C-atoms, Phe is 1,4-phenylene, k1 and k2 are independently of each other 0 or 1, and $R^0$ is H or alkyl with 1 to 4 C atoms.

P is preferably a vinyl group, an acrylate group, a methacrylate group, a propenyl ether group or an epoxy group, especially preferably an acrylate or a methacrylate group.

In another preferred embodiment P is a branched group comprising two or more reactive moieties, like for example a group selected from —OCO—$CR_0$($CH_2$—OCO—CW=$CH_2$)$_2$ and —OCO—C($CH_2$—OCO—CW=$CH_2$)$_3$, with W being H, $C_1$ or $CH_3$ and R being H or alkyl with 1 to 4 C atoms, preferably H or methyl.

As for the spacer group Sp all groups can be used that are known for this purpose to the skilled in the art. The spacer group Sp is preferably a linear or branched alkylene group having 1 to 20 C atoms, in particular 1 to 12 C atoms, in which, in addition, one or more non-adjacent $CH_2$ groups may be replaced by —O—, —S—, —NH—, —N($CH_3$)—, —CO—, —O—CO—, —S—CO—, —O—COO—, —CO—S—, —CO—O—, —CH(halogen)-, —CH(CN)—, —CH=CH— or —C≡C—.

Typical spacer groups are for example —($CH_2$)$_p$—, —($CH_2CH_2O$)$_r$—$CH_2CH_2$—, —$CH_2CH_2$—S—$CH_2CH_2$— or —$CH_2CH_2$—NH—$CH_2CH_2$—, with p being an integer from 2 to 12 and r being an integer from 1 to 3.

Preferred spacer groups are ethylene, propylene, butylene, pentylene, hexylene, heptylene, octylene, nonylene, decylene, undecylene, dodecylene, octadecylene, ethyleneoxyethylene, methyleneoxybutylene, ethylene-thioethylene, ethylene-N-methyliminoethylene, 1-methylalkylene, ethenylene, propenylene and butenylene for example.

Especially preferred are inventive chiral compounds of formula I wherein Sp-X is denoting alkylene or alkylene-oxy with 2 to 6 C atoms. Straight-chain groups are especially preferred.

In another preferred embodiment of the invention the chiral compounds comprise at least one spacer group Sp that is a chiral group of formula IV:

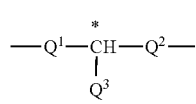

IV wherein $Q^1$ is an alkylene or alkylene-oxy group with 1 to 10 C atoms or a single bond, $Q^2$ is an alkylene or alkylene-oxy group with 1 to 10 C atoms or a single bond, being different from $Q^1$, and $Q^3$ is halogen, a cyano group or an alkyl or alkoxy group with 1 to 4 C atoms different from $Q^2$.

In case $Q^1$ in formula IV is an alkylene-oxy group, the O atom is preferably adjacent to the chiral C atom.

Another preferred embodiment relates to compounds of formula I comprising a photoisomerizable group, for example a group with a C=C, C=N or N=N double bond. These compounds change their shape, for example by E-Z- or cis-trans isomerization, upon photoirradiation e.g. with UV light.

Particularly preferred are photoisomerizable compounds of formula I wherein one or both of $W^1$ and $W^2$ denote -$Z^1$-$A^1$-$(Z^2-A^2)_m$-R and $Z^1$ or $Z^2$ is a photoisomerizable group, in particular —CH=CH—COO— or —OCO—CH=CH—. Very particularly preferred are photoisomerizable compounds of formula I wherein $W^1$ is -$Z^1$-$A^1$-$(Z^2-A^2)_m$-R and $Z^1$ is —OCO—CH=CH—.

Photolysis of photoisomerizable compounds of formula I with e.g. UV light of 360 nm has the effect of isomerising the double bond of the photoisomerizable group from E to Z, thus completely changing the shape of the molecule and hence the physical molecular properties like the twisting power.

The chiral compounds of formula I can be mixed with other mesogenic compounds to give a chiral liquid crystalline mixture. If such a liquid crystalline mixture, for example a cholesteric mixture is coated as a thin layer and aligned on a surface and then photolysed with e.g. UV light of 360 nm, the light changes the shape of the isomerizable dopant—this in turn reduces the HTP, and this has an overall effect of increasing the pitch and thus the reflection wavelength of the mixture. If irradiation is carried out through a photomask towards the layer of the liquid crystalline mixture doped with the chiral photoisomerizable compound, a pattern in the shape of the photomask is obtained, where different regions of the layer show different reflection wavelength. If the photoisomerizable compound and/or the other compounds of the mixture are polymerizable compounds, this pattern can be fixed by in-situ polymerization of the mixture.

As the change of the HTP of the chiral photoisomerizable compound of formula I depends on the intensity of photoradiation, the change of the twist in the mixture can also be controlled by local variation of the radiation intensity, e.g. by the use of grey filters alternatively or in addition to a photomask.

It is also possible to achieve a change of the twist in a direction vertical to the plane of the layer by adding a dye to the mixture that has an absorption maximum at the wavelength where the isomerizable compound shows photoi-somerization, for example a UV dye. The dye will create a gradient in intensity of photoradiation throughout the thickness of the layer, so that the isomerization and thus the change of twist is faster at the top of the layer than at the bottom. In this way a pitch gradient is created, leading to a broadening of the reflected wavelength band. This method is especially useful for the preparation of broadband reflective polarizers.

The chiral photoisomerizable compounds of formula I are thus suitable e.g. for forming patterned films, which can be used for example as reflective polarizers or colour filters for LC displays, for decorative or security applications such as security markings for ID cards, labels or documents of value, in nonlinear optics, for optical recording or information storage.

Particularly preferred compounds of formula I are those of the following formulae

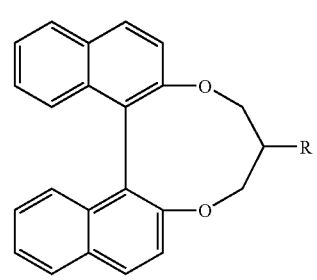

I-1

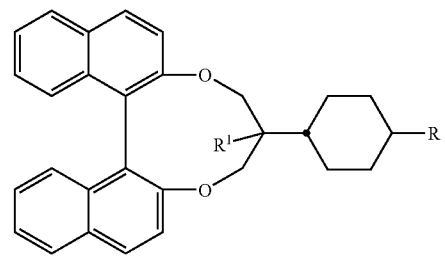

I-2

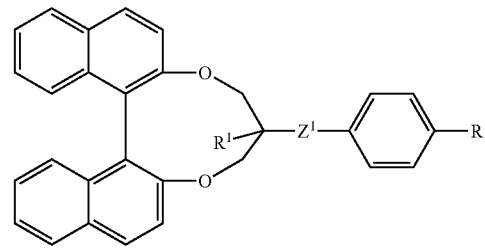

I-3

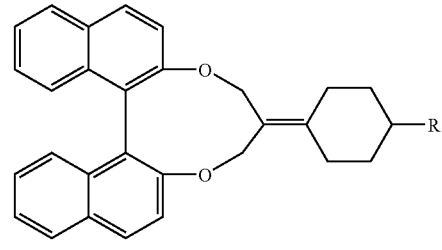

I-4

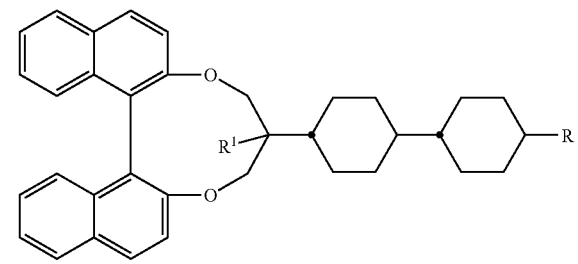

I-5

-continued
I-6
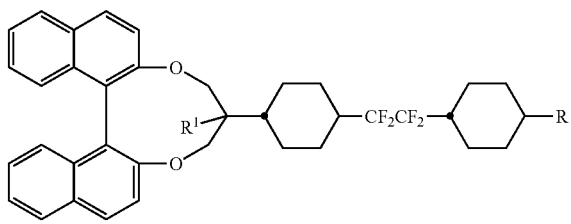
I-7
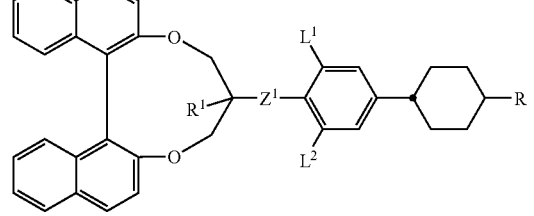
I-8
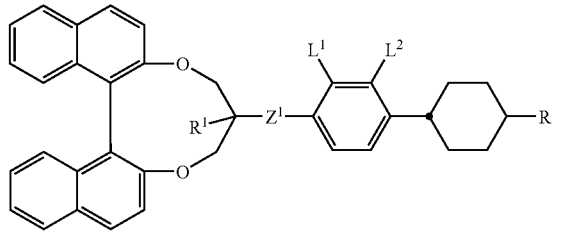
I-9
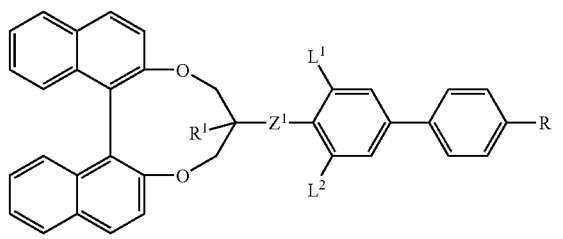
I-10
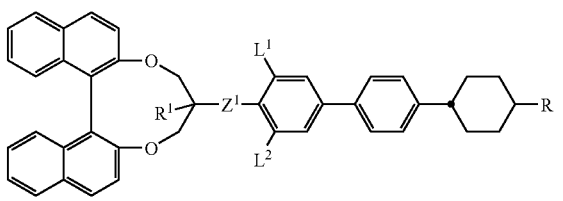
I-11
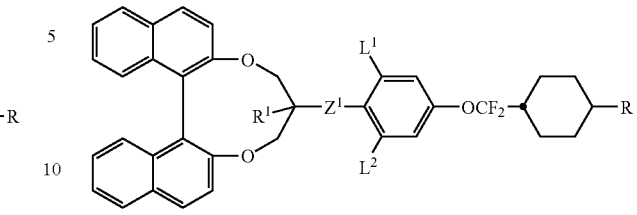
I-12
I-13
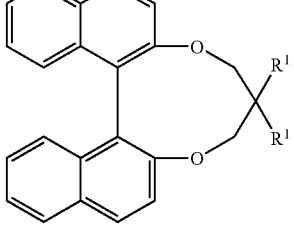
I-14
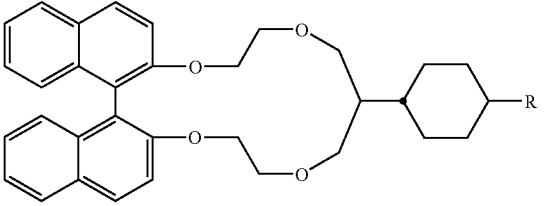
I-15
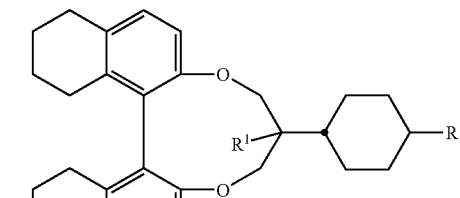
I-16

-continued

I-17
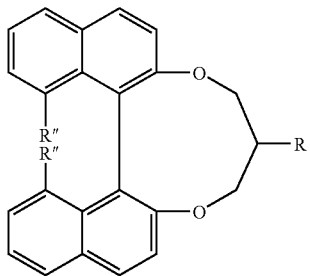

I-18
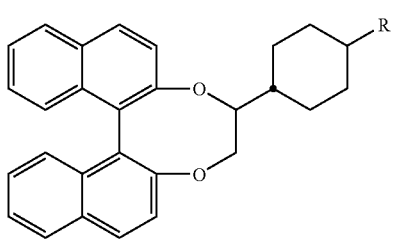

I-19
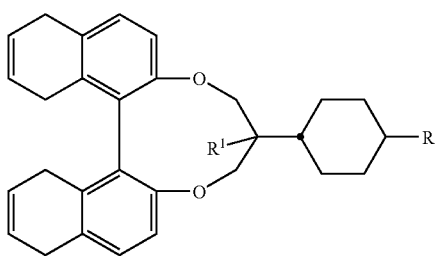

I-20
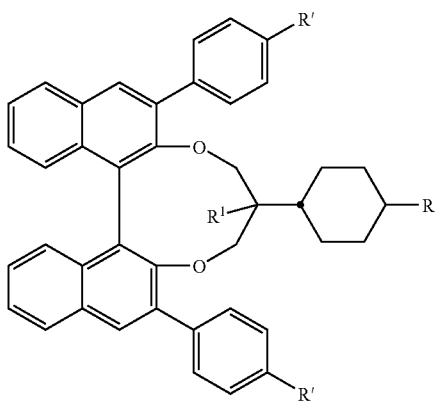

wherein $Z^1$, R and $R^1$ have one of the meanings of formula I, R' and R" have one of the meanings of R in formula I, and $L^1$ and $L^2$ are H or have independently of each other one of the meanings of L in formula I.

In these preferred compounds $L^1$ and $L^2$ are preferably H or F, $R^1$ is preferably H or F, R' and R" are preferably H, F, alkyl or alkoxy with 1 to 12 C atoms or P-Sp-X— as defined above, R" is very preferably $CH_3$, and $Z^1$ is preferably —O—, —OCO—, —COC—CH=CH— or a single bond.

Particularly preferred compounds of formula I-3 are those of the following subformulae I-3a
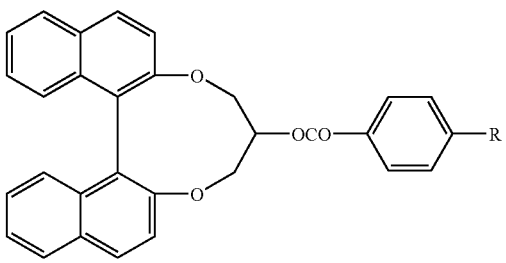

I-3b
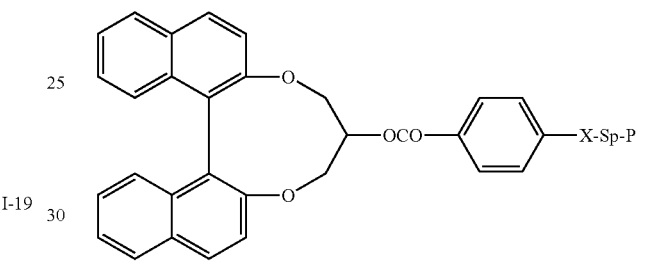

I-3c
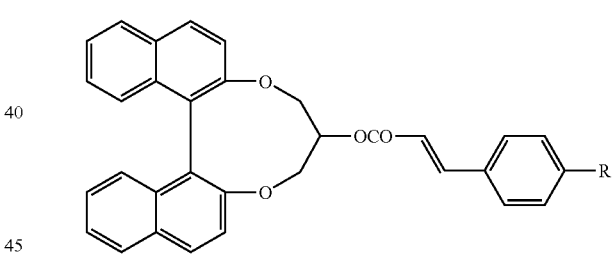

I-3d
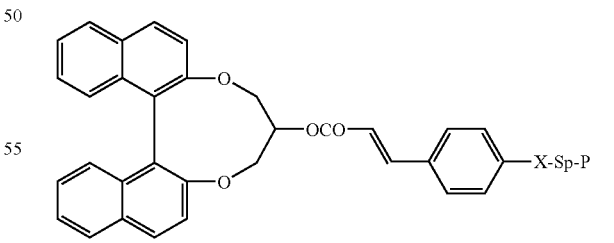

wherein R, X. Sp and P have the meanings given above.

The inventive chiral compounds can be synthesized according to or in analogy to known methods, as described for example in J. J. G. S. van Es, A. M. Biemans and E. W. Meijer, Tetrahedron: Asymmetry, 1997, 8, 1825-183. In particular, they can be prepared according to or in analogy to the following reaction schemes. Further methods for preparing the inventive compounds can be taken from the examples.

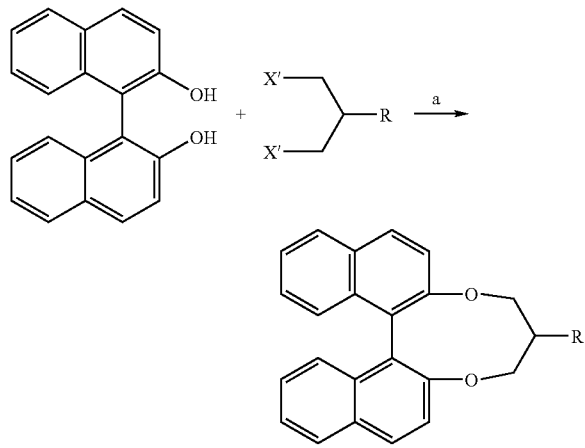

Scheme 1 a) DMF, K$_2$CO$_3$, 80° C.
X'=Br, OTs

The Synthesis of 5,6,7,8,5',6',7',8'-Octahydro-1,1'-binaphthyl-2,2'-diol is described for example in D. J. Cram et al., J. Org. Chem. 1978, 43, 1939-1946.

The chiral compounds of formula I can be used in a liquid crystal mixture for displays exhibiting a helically twisted molecular structure of the liquid crystal matrix like, for example, TN displays of the active or passive matrix type, STN, phase-change, guest-host, ferroelectric or cholesteric displays like SSCT (surface stabilized cholesteric texture) or PSCT (polymer stabilized cholesteric texture).

Thus, another object of the invention is a liquid crystal mixture, in particular a chiral smectic or cholesteric liquid crystal mixture, comprising at least one chiral compound of formula I.

Yet another object of the invention is a liquid crystal display comprising a liquid crystal medium containing at least one chiral compound of formula I.

The chiral compounds of formula I are characterized by high values of the HTP. This enables the preparation of liquid crystal mixtures with a high helical twist, i.e. a low pitch, by using only low amounts of chiral compounds of formula I. This is a considerable advantage, as it is often observed that the addition of high amounts of chiral dopants to a liquid crystal mixture negatively affects its liquid crystal phase behaviour and electrooptical properties, such as the dielectric anisotropy, the viscosity or the clearing point. Thus, by using chiral compounds of formula I in a liquid crystal mixture or display its properties are altered only to a minor extent, compared to prior art dopants, resulting for example in a lower threshold voltage and faster switching times of the display.

The chiral compounds of formula I are further characterized by a high solubility in a liquid crystal host mixture. Undesired spontaneous crystallization at low temperatures is reduced, and the operating temperature range of the mixture can be broadened. The use of a second dopant, which is often added to avoid crystallization, can thus be avoided.

A particularly preferred embodiment of the present invention therefore relates to a liquid crystal mixture comprising only one chiral compound, which is a compound of formula I, and to a display comprising such a mixture.

The chiral compounds of formula I also show a low temperature dependence of the HTP when added to a liquid crystal host mixture. They are thus useful as chiral dopants for liquid crystal mixtures and displays with a low temperature dependence of the pitch.

A liquid crystal mixture according to the invention comprises preferably 0.1 to 30%, in particular 1 to 25% and very particularly preferably 2 to 15% by weight of chiral compounds of formula I. It preferably comprises 1, 2 or 3 chiral compounds of formula I.

The compounds of formula I are especially suitable for use in cholesteric liquid crystal mixtures for cholesteric displays, in particular SSCT or PSCT displays. Cholesteric displays are described for example in WO 92/19695, WO 93/23496, U.S. Pat. No. 5,453,863 or U.S. Pat. No. 5,493,430, the entire disclosure of these documents being introduced into this application by way of reference.

It was found that when using chiral compounds of formula I as dopants in cholesteric liquid crystal media, for SSCT or PSCT display, they exhibit good solubility in the nematic host mixture and induce a high helical twist with low temperature dependence of the helical pitch and the reflection wavelength. Cholesteric mixtures with high brightness of the reflection colour and low temperature dependence can be achieved even by using only one chiral dopant according to formula I, preferably in low amounts. This is a considerable advantage over prior art, where high amounts of dopants are needed, and where it is often necessary to use two or more dopants with opposite temperature dependence of the helical twist (e.g. one with positive temperature dependence and one with negative temperature dependence) to achieve good temperature compensation of the reflection wavelength.

Thus, a particularly preferred embodiment of the present invention relates to a cholesteric liquid crystal medium, in particular for use in SSCT and PSCT displays, comprising one chiral dopant, which is a compound of formula I, preferably in an amount of 15% or less, in particular 10% or less, very preferably 5% or less.

For the applications described above the liquid crystal mixture preferably contains a chiral component which contains at least one chiral compound of formula I, and a nematic component comprising one or more nematic or nematogenic compounds.

Preferably the liquid crystal mixture consists of 2 to 25, preferably 3 to 15 compounds, at least one of which is a chiral compound of formula I. The other compounds, forming the nematic component, are preferably low molecular weight liquid crystal compounds selected from nematic or nematogenic substances, for example from the known classes of the azoxybenzenes, benzylidene-anilines, biphenyls, terphenyls, phenyl or cyclohexyl benzoates, phenyl or cyclohexyl esters of cyclohehexanecarboxylic acid, phenyl or cyclohexyl esters of cyclohexylbenzoic acid, phenyl or cyclohexyl esters of cyclohexylcyclohexanecarboxylic acid, cyclohexylphenyl esters of benzoic acid, of cyclohexanecarboxylic acid and of cyclohexylcyclohexanecarboxylic acid, phenylcyclohexanes, cyclohexylbiphenyls, phenylcyclohexylcyclohexanes, cyclohexylcyclohexanes, cyclohexylcyclohexenes, cyclohexylcyclohexylcyclohexenes, 1,4-bis-cyclohexylbenzenes, 4,4'-bis-cyclohexylbiphenyls, phenyl- or cyclohexylpyrimidines, phenyl- or cyclohexylpyridines, phenyl- or cyclohexylpyridazines, phenyl- or cyclohexyldioxanes, phenyl- or cyclohexyl-1,3-dithianes, 1,2-diphenyl-ethanes, 1,2-dicyclohexylethanes, 1-phenyl-2-cyclohexylethanes, 1-cyclohexyl-2-(4-phenylcyclohexyl)-ethanes, 1-cyclohexyl-2-biphenyl-ethanes, 1-phenyl 2-cyclohexylphenylethanes, optionally halogenated stilbenes, benzyl phenyl ether, tolanes, substituted cinnamic acids and further classes of nematic or nematogenic substances. The 1,4-phenylene groups in these compounds may also be laterally mono- or difluorinated.

The liquid crystal mixture of this preferred embodiment is based on the achiral compounds of this type.

The most important compounds that are possible as components of these liquid crystal mixtures can be characterized by the following formula

R'-L'-G'-E-R"

wherein $L^1$ and E, which may be identical or different, are in each case, independently from one another, a bivalent radical from the group formed by -Phe-, -Cyc-, -Phe-Phe-, -Phe-Cyc-, -Cyc-Cyc-, -Pyr-, -Dio-, —B-Phe- and —B-Cyc- and their mirror images, where Phe is unsubstituted or fluorine-substituted 1,4-phenylene, Cyc is trans-1,4-cyclohexylene or 1,4-cyclohexenylene, Pyr is pyrimidine-2,5-diyl or pyridine-2,5-diyl, Dio is 1,3-dioxane-2,5-diyl and B is 2-(trans-1,4-cyclohexyl)ethyl, pyrimidine-2,5-diyl, pyridine-2,5-diyl or 1,3-dioxane-2,5-diyl.

G' in these compounds is selected from the following bivalent groups —CH=CH—, —N(O)N—, —CH=CY—, —CH=N(O)—, —C≡C—, —CH$_2$—CH$_2$—, —CO—O—, —CH$_2$—O—, —CO—S—, —CH$_2$—S—, —CH=N—, —COO-Phe-COO— or a single bond, with Y being halogen, preferably chlorine, or —CN.

R' and R" are, in each case, independently of one another, alkyl, alkenyl, alkoxy, alkenyloxy, alkanoyloxy, alkoxycarbonyl or alkoxycarbonyloxy with 1 to 18, preferably 3 to 12 C atoms, or alternatively one of R' and R" is F, $CF_3$, $OCF_3$, Cl, NCS or CN.

In most of these compounds R' and R" are, in each case, independently of each another, alkyl, alkenyl or alkoxy with different chain length, wherein the sum of C atoms in nematic media generally is between 2 and 9, preferably between 2 and 7.

Many of these compounds or mixtures thereof are commercially available. All of these compounds are either known or can be prepared by methods which are known per se, as described in the literature (for example in the standard works such as Houben-Weyl, Methoden der Organischen Chemie [Methods of Organic Chemistry], Georg-Thieme-Verlag, Stuttgart), to be precise under reaction conditions which are known and suitable for said reactions. Use may also be made here of variants which are known per se, but are not mentioned here.

Polymerizable compounds of formula I or polymerizable liquid crystal mixtures comprising one or more compounds of formula I are useful for the preparation of polymerizable mixtures, which can be used for example in polymer stabilized liquid crystal displays, such as PSCT (polymer stabilized cholesteric texture) and anisotropic polymer gels, which can be used for example in scattering type displays. Anisotropic polymer gels and displays comprising them are disclosed for example in DE 195 04 224 and GB 2 279 659.

The chiral compounds of formula I and polymerizable liquid crystal mixtures comprising them are particularly useful for the preparation of anisotropic polymer films with helically twisted molecular structure with uniform planar orientation, i.e. wherein the helical axis is oriented perpendicular to the plane of the film.

For example, oriented cholesteric polymer films can be used as broad waveband reflective polarizers like for example described in EP 0 606 940, as colour filters, for security markings, or for the preparation of liquid crystal pigments for decorative or security uses.

For the preparation of anisotropic polymer gels or oriented polymer films, the liquid crystal mixture should comprise at least one polymerizable compound, which can be a compound of formula I or an additional polymerizable mesogenic or liquid crystalline compound.

Thus, another object of the invention are polymerizable liquid crystal mixtures comprising at least one chiral compound of formula I.

Examples of suitable polymerizable mesogenic compounds that can be used as components of the polymerizable liquid crystal mixture, are disclosed for example in WO 93/22397; EP 0,261,712; DE 195,04,224; WO 95/22586 and WO 97/00600. The compounds disclosed in these documents, however, are to be regarded merely as examples that shall not limit the scope of this invention.

Preferably the polymerizable liquid crystal mixture comprises at least one polymerizable mesogenic compound having one polymerizable functional group and at least one polymerizable mesogenic compound having two or more polymerizable functional groups.

Examples of especially useful monoreactive chiral and achiral polymerizable mesogenic compounds are shown in the following list of compounds, which should, however, be taken only as illustrative and is in no way intended to restrict, but instead to explain the present invention:

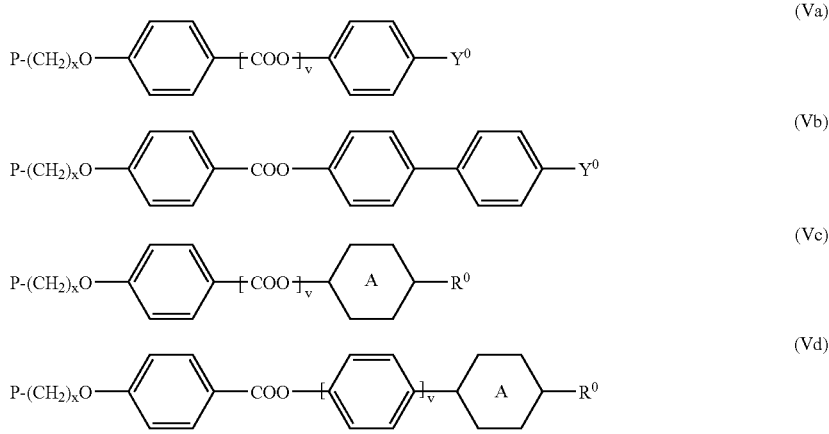

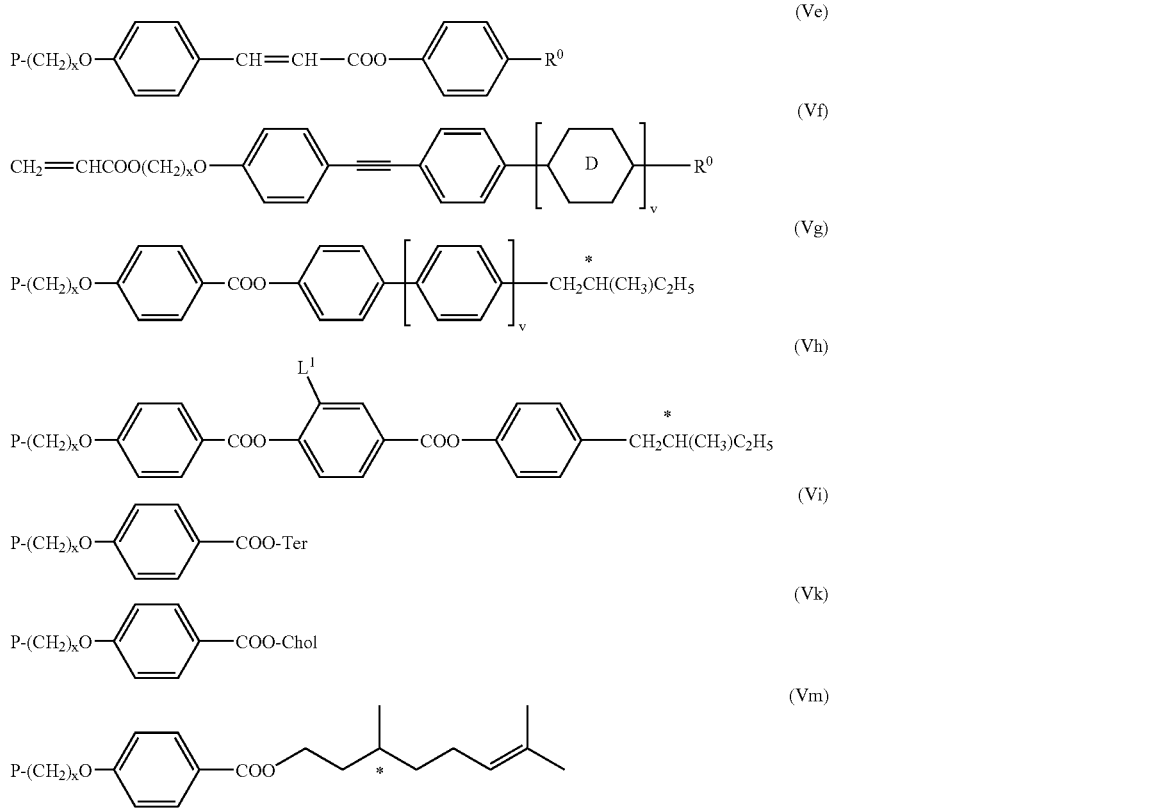

wherein, P has one of the meanings given above, x is an integer from 1 to 12, A and D are 1,4-phenylene or 1,4-cyclohexylene, v is 0 or 1, $Y^0$ is a polar group, $R^0$ is an unpolar alkyl or alkoxy group, Ter is a terpenoid radical like e.g. menthyl, Chol is a cholesteryl group, and $L^1$ and $L^2$ are each independently H, F, Cl, CN, OH, $NO_2$ or an optionally halogenated alkyl, alkoxy or carbonyl group with 1 to 7 C atoms.

The polar group $Y^0$ is preferably CN, $NO_2$, halogen, $OCH_3$, OCN, SCN, $COR^5$, $COOR^5$ or a mono- oligo- or polyfluorinated alkyl or alkoxy group with 1 to 4 C atoms. $R^5$ is optionally fluorinated alkyl with 1 to 4, preferably 1 to 3 C atoms.

Especially preferably the polar group $Y^0$ is selected of F, Cl, CN, $NO_2$, $OCH_3$, $COCH_3$, $COC_2H_5$, $COOCH_3$, $COOC_2H_5$, $CF_3$, $C_2F_5$, $OCF_3$, $OCHF_2$, and $OC_2F_5$, in particular F, Cl, CN, $OCH_3$ and $OCF_3$.

The unpolar group $R^0$ is preferably an alkyl group with 1 or more, preferably 1 to 15 C atoms or an alkoxy group with 2 or more, preferably 2 to 15 C atoms.

Examples of useful direactive chiral and achiral polymerizable mesogenic compounds are shown in the following list of compounds, which should, however, be taken only as illustrative and is in no way intended to restrict, but instead to explain the present invention

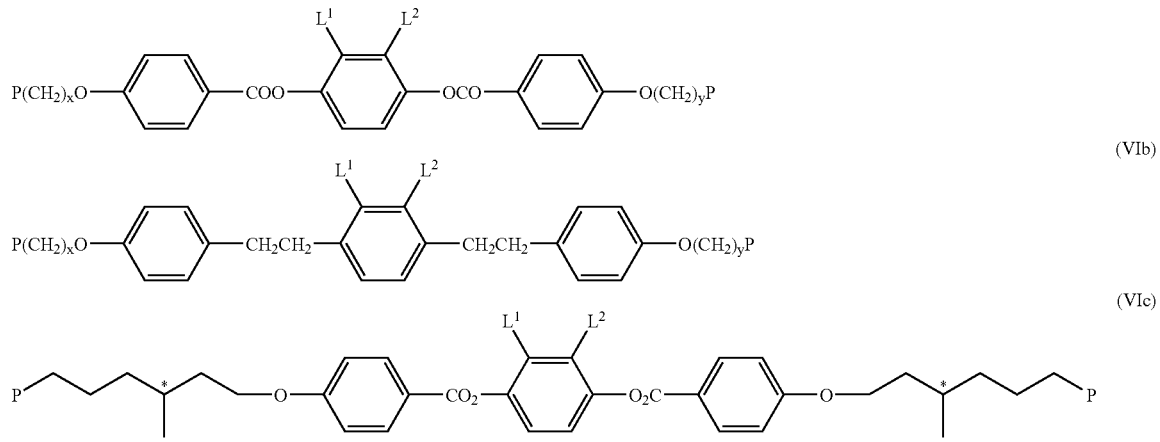

-continued

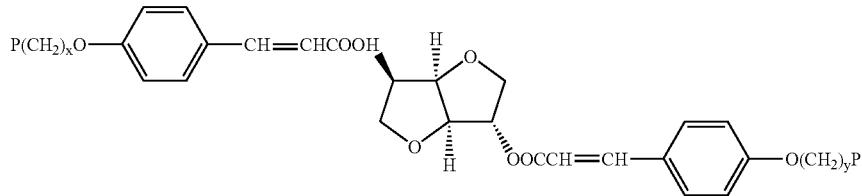
(VId)

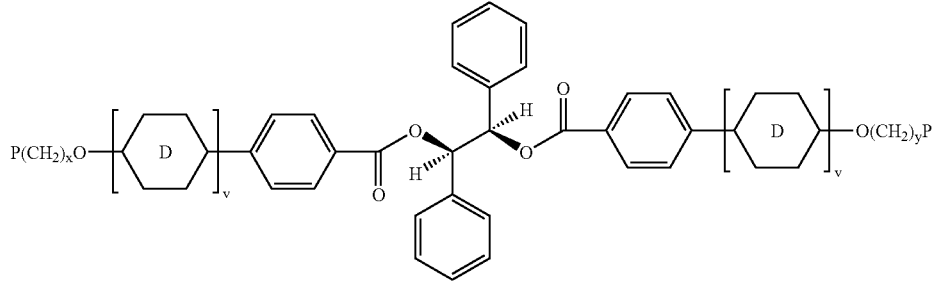
(VIe)

wherein P, x, D, $L^1$ and $L^2$ have one of the meanings given above and y is an integer from 1 to 12 the same as or different from x.

A polymerizable liquid crystal material according to the first preferred embodiment as described above comprises one or more chiral dopants which themselves do not necessarily have to show a liquid crystal phase and give good planar alignment themselves, in particular non-polymerizable chiral dopants.

The mono- and difunctional polymerizable mesogenic compounds of above formulae V and VI can be prepared by methods which are known per se and which are described in the documents cited above and, for example, in standard works of organic chemistry such as, for example, Houben-Weyl, Methoden der organischen Chemie, Thieme-Verlag, Stuttgart.

In a preferred embodiment of the invention the polymerizable liquid crystal mixtures comprise at least one inventive chiral compound, at least one monofunctional compound of formulae Va-Vm and at least one bifunctional polymerizable compound of formulae VIa-VIe.

In another preferred embodiment the polymerizable liquid crystal mixtures comprise at least one inventive chiral compound and at least two monofunctional compounds of formulae Va-Vm.

Another object of the invention is an anisotropic polymer film with an oriented chiral liquid crystalline phase obtainable by (co)polymerizing a liquid crystal mixture comprising at least one chiral compound of formula I and at least one polymerizable mesogenic compound preferably selected of formula Va-Vm and VIa-VIe and/or at least one polymerizable chiral compound of formula I.

To prepare anisotropic polymer film with a chiral liquid crystalline phase with uniform orientation the polymerizable liquid crystal can be coated onto a substrate, aligned and polymerized in situ, for example by exposure to heat or actinic radiation, to fix the uniform orientation of the liquid crystal molecules. Alignment and curing are carried out in the liquid crystalline phase of the mixture.

Actinic radiation means irradiation with light, like UV light, IR light or visible light, irradiation with X-rays or gamma rays or irradiation with high energy particles, such as ions or electrons. As a source for actinic radiation for example a single UV lamp or a set of UV lamps can be used. Another possible source for actinic radiation is a laser, like e.g. a UV laser, an IR laser or a visible laser.

For example, when polymerizing by means of UV light, a photoinitiator can be used that decomposes under UV irradiation to produce free radicals or ions that start the polymerization reaction.

It is also possible to use a cationic photoinitiator, when curing reactive mesogens with for example vinyl and epoxide reactive groups, that photocures with cations instead of free radicals.

As a photoinitiator for radical polymerization for example the commercially available Irgacure 651, Irgacure 184, Darocure 1173 or Darocure 4205 (all from Ciba Geigy AG) can be used, whereas in case of cationic photopolymerization the commercially available UVI 6974 (Union Carbide) can be used.

Preferably the polymerizable liquid crystal mixture comprising polymerizable chiral compounds of formula I and/or polymerizable mesogenic compounds of formulae V and VI additionally comprises 0.01 to 10%, in particular 0.05 to 8%, very preferably 0.1 to 5% by weight of a photoinitiator, especially preferably a UV-photoinitiator.

Polymerization is preferably carried out under an atmosphere of inert gas, preferably under a nitrogen atmosphere.

As a substrate for example a glass or quarz sheet as well as a plastic film or sheet can be used. It is also possible to put a second substrate on top of the coated mixture prior to, during and/or after polymerization. The substrates can be removed after polymerization or not. When using two substrates in case of curing by actinic radiation, at least one substrate has to be transmissive for the actinic radiation used for the polymerization.

Isotropic or birefringent substrates can be used. In case the substrate is not removed from the polymerized film after polymerization, preferably isotropic substrates are used.

Preferably at least one substrate is a plastic substrate such as for example a film of polyester such as polyethyleneterephthalate (PET), of polyvinylalcohol (PVA), polycarbonate (PC) or triacetylcellulose (TAC), especially preferably a PET film or a TAC film. As a birefringent substrate for example an uniaxially stretched plastic film can be used. For example PET films are commercially available from ICI Corp. under the trade name Melinex.

Preferably the polymerizable liquid crystal mixture I is coated as a thin layer on a substrate or between substrate, and aligned in its chiral mesophase into planar orientation, wherein the axis of the molecular helix extends transversely to the layer.

Planar orientation can be achieved for example by shearing the mixture, e.g. by means of a doctor blade. It is also possible to put a second substrate on top of the coated material. In this case, the shearing caused by putting together the two substrates is sufficient to give good alignment. Alternatively it is possible to apply an alignment layer, for example a layer of rubbed polyimide or sputtered $SiO_x$, on top of at least one of the substrates, or to apply an electric or magnetic field to the coated mixture, in order to induce or enhance planar alignment. In a preferred method planar alignment is induced or enhanced by addition of one or more surface-active compounds to the polymerizable mixture.

In some cases it is of advantage to apply a second substrate not only to aid alignment of the polymerizable mixture but also to exclude oxygen that may inhibit the polymerization. Alternatively the curing can be carried out under an atmosphere of inert gas. However, curing in air is also possible using suitable photoinitiators and high lamp power. When using a carbonic photoinitiator oxygen exclusion most often is not needed, but water should be excluded.

A detailed description of the in situ polymerization of polymerizable mesogenic compounds can be found in D. J. Broer et al., Makromolekulare Chemie 190, 2255 (1989).

A polymerizable liquid crystal mixture for the preparation of anisotropic polymer films comprises preferably 0.1 to 35%, in particular 0.5 to 15% and very particularly preferably 0.5 to 5% by weight of one or more polymerizable chiral compounds of formula I.

Polymerizable liquid crystal mixtures are preferred that comprise 1 to 3 chiral compounds of formula I.

The inventive polymerizable liquid crystal mixtures can additionally comprise one or more other suitable components, such as, for example, catalysts, sensitizers, stabilizers, co-reacting monomers or surface-active compounds.

In a preferred embodiment of the invention, the inventive polymerizable liquid crystal mixture comprises a stabilizer that is used to prevent undesired spontaneous polymerization for example during storage of the composition. As stabilizers in principal all compounds can be used that are known to the skilled in the art for this purpose. These compounds are commercially available in a broad variety. Typical examples for stabilizers are 4-ethoxyphenol or butylated hydroxytoluene (BHT).

It is also possible, in order to increase crosslinking of the polymers, to add up to 20% of a non mesogenic compound with two or more polymerizable functional groups to the polymerizable composition alternatively or additionally to the multifunctional polymerizable mesogenic compounds.

Typical examples for difunctional non mesogenic monomers are alkyldiacrylates or alkyldimethacrylates with alkyl groups of 1 to 20 C atoms. Typical examples for non mesogenic monomers with more than two polymerizable groups are trimethylpropanetrimethacrylate or pentaerythritoltetraacrylate.

Polymerization of inventive compositions comprising compounds with only one polymerizable functional group leads to linear polymers, whereas in the presence of compounds with more than one polymerizable functional group crosslinked polymers are obtained.

For the preparation of anisotropic polymer gels, the liquid crystal mixtures can be polymerized in situ as described above, however, in this case alignment of the polymerizable mixture is not necessary.

The inventive chiral compounds of formula I and liquid crystal mixtures, liquid crystal polymers or liquid crystal pigments comprising them are also suitable for use in cosmetic and pharmaceutical compositions, for example for coloured make-up as described in EP 815 826 or as UV-filters for the protection of human skin or hair, in particular protection against UV-A and UV-B-radiation, as described for example in DE 196 29 761 or EP 1 038 941. The inventive dopants have a high HTP, therefore only small amounts are needed to yield a short pitch, resulting in a material that shows reflection in the UV range and is suitable as UV-filter.

A liquid crystal mixture, liquid crystal polymer or liquid crystal pigment comprising a chiral compound of formula I and reflecting UV light, in particular of a wavelength of 200 to 400 nm, is another object of the invention. Another object is a cosmetic composition, in particular a cosmetic or pharmaceutical composition for protection of human skin or hair, comprising as UV-filter a liquid crystal mixture, liquid crystal polymer or liquid crystal pigment comprising a chiral compound of formula I and reflecting UV light, in particular in a wavelength range of 200-440 nm, especially 280-400 nm, 200-230 nm (UV-C) and 280-330 nm (UV-B).

From the foregoing description, one skilled in the art can easily ascertain the essential characteristics of this invention, and without departing from the spirit and scope thereof, can make various changes and modifications of the invention to adapt it to various usages and conditions.

Without further elaboration, it is believed that one skilled in the art can, using the preceding description, utilize the present invention to its fullest extent. The following examples are, therefore, to be construed as merely illustrative and not limitative of the remainder of the disclosure in any way whatsoever.

In the foregoing and in the following examples, unless otherwise indicated, all temperatures are set forth uncorrected in degrees Celsius and all parts and percentages are by weight.

In the present patent application and in the following examples all chemical structures of LC compounds are given by acronyms the transformation of which into chemical formulae is done as shown in the following. All residues $C_nH_{2n+1}$ and $C_mH_{2m+1}$ are straight-chained alkyl groups with n resp. m carbon atoms. The code of Table B is self-explanatory. In Table A only the acronym for the core structure is given. In a concrete this acronym is followed by a dash and a code for the substituents $R^1$, $R^2$, $L^1$ and $L^2$ as follows:

| Code für $R^1$, $R^2$, $L^1$, $L^2$, $L^3$ | $R^1$ | $R^2$ | $L^1$ | $L^2$ | $L^3$ |
|---|---|---|---|---|---|
| nm | $C_nH_{2n+1}$ | $C_mH_{2m+1}$ | H | H | H |
| nOm | $C_nH_{2n+1}$ | $C_mH_{2m+1}$ | H | H | H |
| n | $C_nH_{2n+1}$ | CN | H | H | H |
| nN•F | $C_nH_{2n+1}$ | CN | H | H | F |

TABLE A

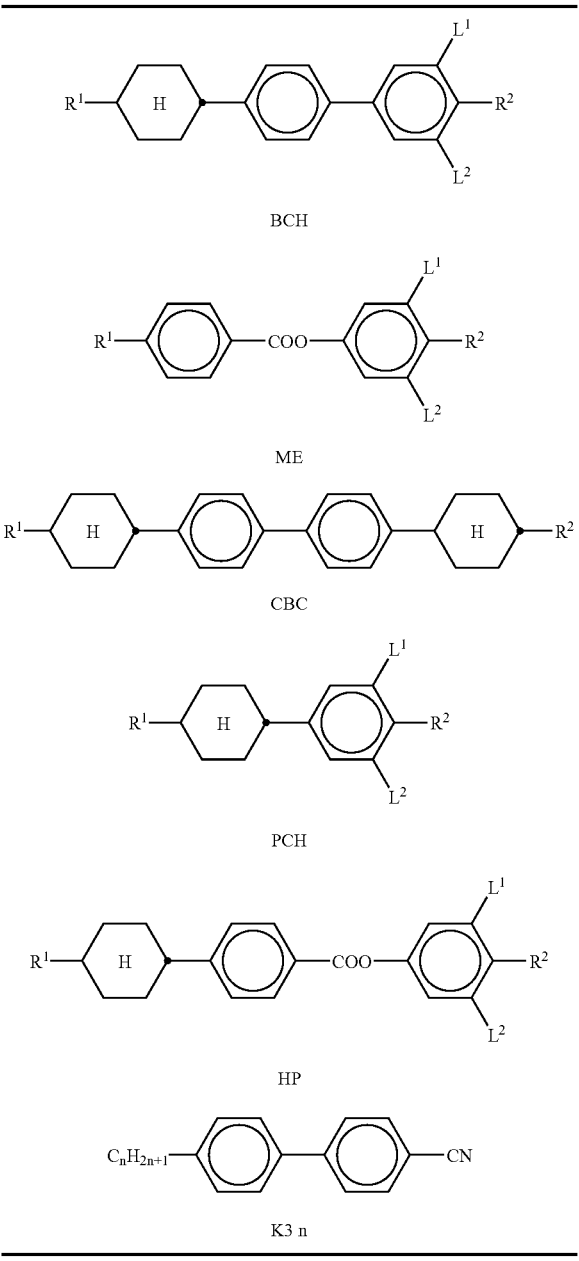

BCH

ME

CBC

PCH

HP

K3 n

TABLE B

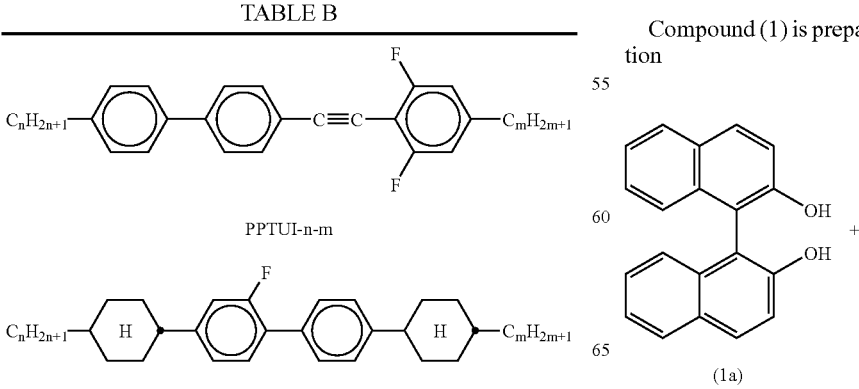

PPTUI-n-m

TABLE B-continued

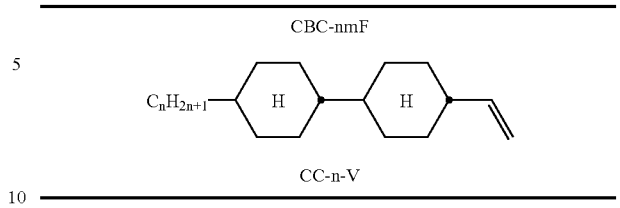

CBC-nmF

CC-n-V

The following abbreviations are used

Δn denotes the optical anisotropy measured at 20° C. and 589 nm $n_e$ denotes the extraordinardy refractive index at 20° C. and 589 nm Δε denotes the dielectric anisotropy at 20° C.

$\varepsilon_\parallel$ denotes the dielectric constant in the parallel direction to the molecular axis Kp denotes the clearing point [° C.]

$\gamma_1$ denotes the rotational viscosity [mPa s]

Δλ denotes the maximum variation of the reflection wavelength [nm] within a given temperature range, or between −20° C. and +70 ° C. unless stated ortherwise The values of the helical twisting power HTP of a chiral compound in a liquid crystalline host are given according to the equation HTP=$(p \cdot c)^{-1}$ in $\mu m^{-1}$, wherein p is the pitch of the molecular helix, given in μm, and c is the concentration by weight of the chiral compound in the host given in relative values (thus, e.g. a concentration of 1% by weight is corresponding to a value of c of 0.01). Unless stated otherwise, the HTP values were determined in the commercially available liquid crystal host mixture MLC-6260 (Merck KGbA, Darmstadt, Germany) at a concentration of 1% and a temperature of 20° C.

The following abbreviations are used to illustrate the liquid crystalline phase behaviour of the compounds: C=crystalline; N=nematic; S=smectic; N*, Ch=chiral nematic or cholesteric; I=isotropic. The numbers between these symbols indicate the phase transition temperatures in degree Celsius.

C* in a chemical formula denotes a chiral C atom. DCM is dichloromethane. "Conventional workup" means: water is added if necessary, the mixture is extracted with methylene chloride, diethyl ether or toluene, the phases are separated, the organic phase is dried and concentrated by evaporation, and the product is purified by crystallization and/or chromatography:

EXAMPLE 1

Compound (1) is prepared according to the following reaction (1a)

-continued

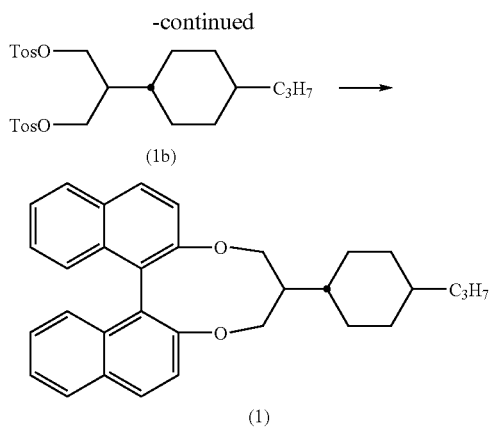

5 g (14.5 mmol) (–)-S-Binaphthol (1a) and 2.7 g (19.2 mmol) potassium carbonate in 100 ml DMF were heated to 80° C. and 10.66 g (21 mmol) of the tosylate (1b) were added dropwise. After stirring for 20 h the reactive mixture was poured onto 500 ml water and 300 ml MTB-ether. After conventional workup 3.8 g (40.8%) of (1) were obtained as colourless crystals with a melting point of 158° C. and a HTP of 104.

EXAMPLE 2

Compound (2) is prepared in analogy to example 1

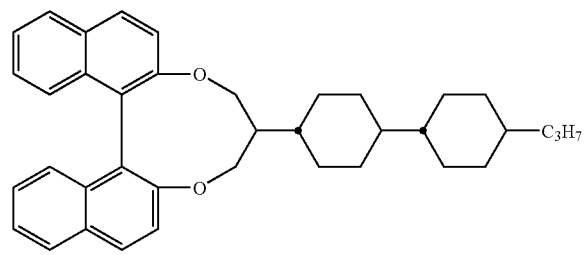

and has a melting point of 214° C. and a HTP of 91.

EXAMPLE 3

Compound (3) is prepared in analogy to example 1

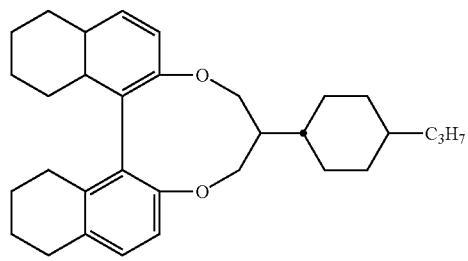

EXAMPLE 4

Compound (4) is prepared as follows.

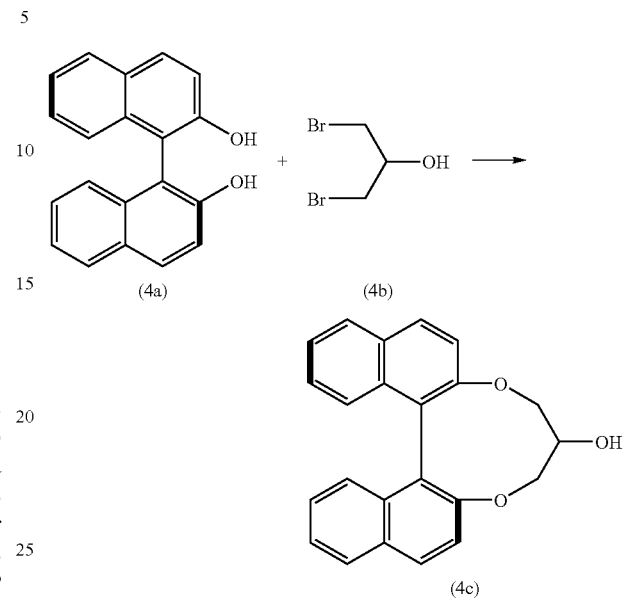

(S)-(–)-1,1'-binaphthyl-2,2'-diol (20.0 g, 0.070 mol) and potassium carbonate (21.2 g, 0.152 mol) were dissolved in DMF (200 ml) and heated at 80° C. Then, 1,3-dibromo-2-propanol, (17.6 g, 0.077 mol) in DMF (100 ml) were added dropwise within 1 h. The reaction was stirred for 24 h at 80° C. and then poured onto water (1 l) and ether (250 ml). The aqueous layer was separated and extracted with ether. The combined org. layers were washed thrice with 2 M sodium hydroxide and twice with water and dried ($Na_2SO_4$). The solvent was evaporated and the crude product was filtered through silica with touluene/ethyl acetate (10:1) to give 9.06 g (33%) of crude product (4c) as a yellow foam, which was reacted without further purification (HPLC: 96%).

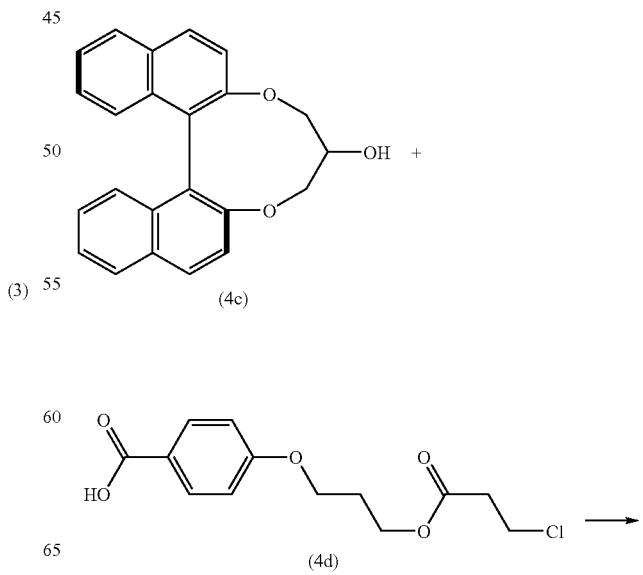

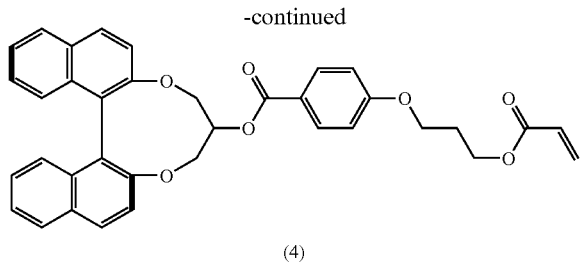

(4)

To a suspension of (S)-BINOL ether (4c) (2.85 g, 8.32 mmol), carboxylic acid (4d) (2.39 g, 8.32 mmol) and 4-(N,N-dimethylamino)pyridine (51 mg, 0.52 mmol, 5 mol %) in toluene (20 ml), a solution of dicyclohexylcarbodiimid (2.06 g, 10.0 mmol) in toluene (10 ml) was added dropwise. The reaction was allowed to stirr at room temp. for 2 d and was then filtered. The filtrate was evaporated and the residue was purified by column chromatography (petrol/ethyl acetate, 5:2) on silica. The crude product was dissolved in dichloromethane (30 ml), triethylamine (1.9 ml, 13.5 mmol) was added and the reaction was heated at 40° C. for 20 h. The mixture was the poured onto ether (100 ml), washed with water and dried ($Na_2SO_4$). The solvent was removed in vacuo and the residue was purified by column chromatography on silica (toluene/ethyl acetate, 10:1) to give 3.00 g (62%, 2 steps) of binol acrylate (4) as a colourless foam.

$^1$H NMR ($CDCl_3$, 500 MHz) and $^{13}$C NMR ($CDCl_3$, 100 MHz) gave the expected signals.

Compound (4) has a HTP of 75, measured in the commercially available nematic host mixture. BL 087 (from Merck Ltd., Poole, UK).

EXAMPLE 5

Compound (5) is prepared in analogy to example 4.

$^1$H NMR ($CDCl_3$, 500 MHz) and $^{13}$C NMR ($CDCl_3$, 100 MHz) gave the expected signals.

Compound (5 has a HTP of 71, measured in the commercially available nematic host mixture BL 087 (from Merck Ltd., Poole, UK).

EXAMPLE 6

Compound (6) is prepared in analogy to example 4.

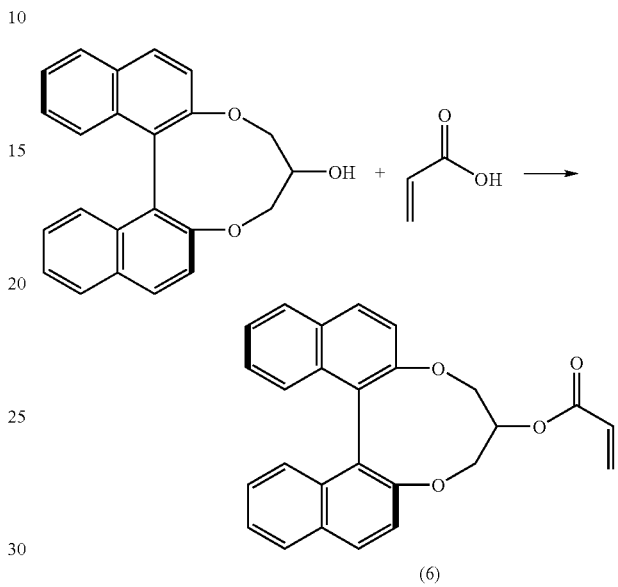

(6)

$^1$H NMR ($CDCl_3$, 500 MHz) and $^{13}$C NMR ($CDCl_3$, 100 MHz) gave the expected signals.

Compound (6) has a melting point of 176° C. and a HTP of 73, measured in the commercially available nematic host mixture BL 087 (from Merck Ltd., Poole, UK).

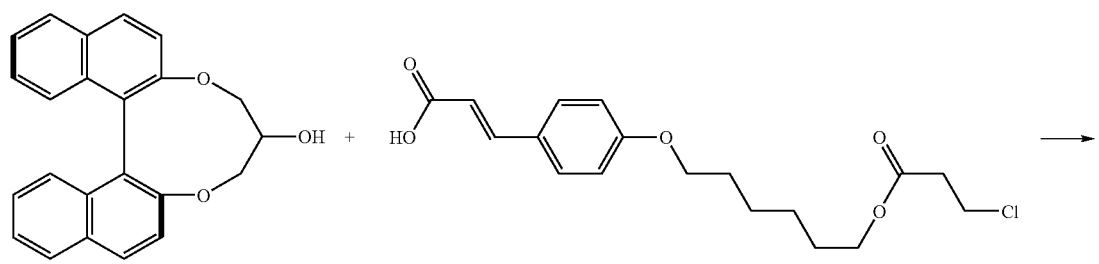

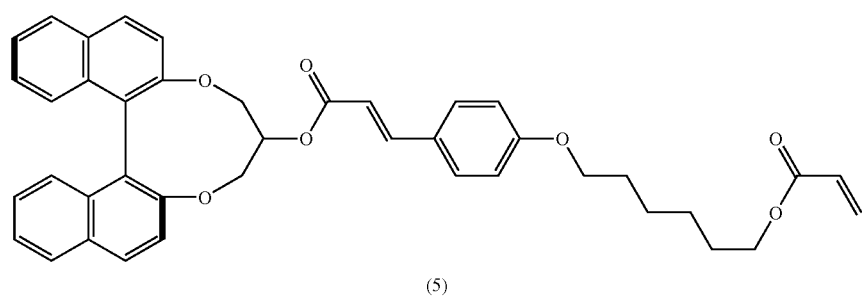

(5)

EXAMPLE 7

Compound (7) is prepared in analogy to example 4.

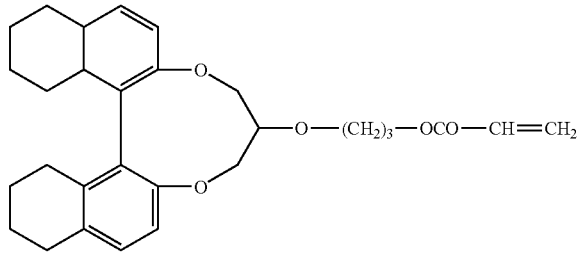

(7)

Compound (7) has a melting point of 120° C. and a HTP of 51.9.

EXAMPLE 8

Compound (8) was prepared by reaction of compound (1) with TMEDA and BuLi (15% in n-Hexan) in diethyl ether, followed by addition of 1-iodo pentane in n-pentane, and conventional workup according to the following reaction scheme.

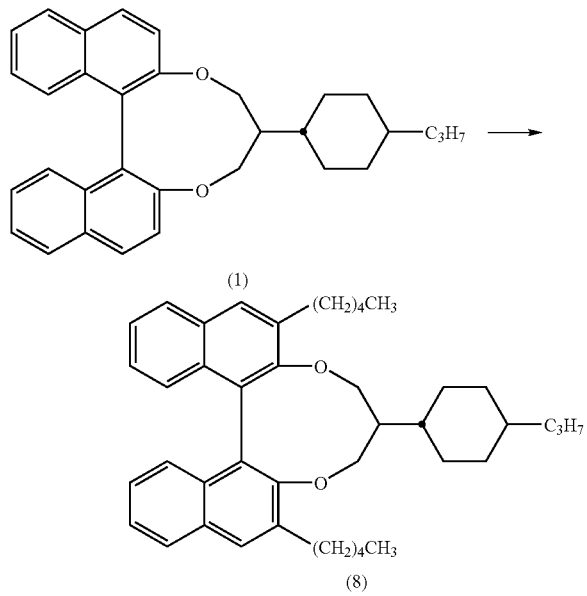

Compound (8) has a melting point of 84° C. and a HTP of 28.7.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various conditions and usages.

The invention claimed is:
1. A chiral compound of formula I

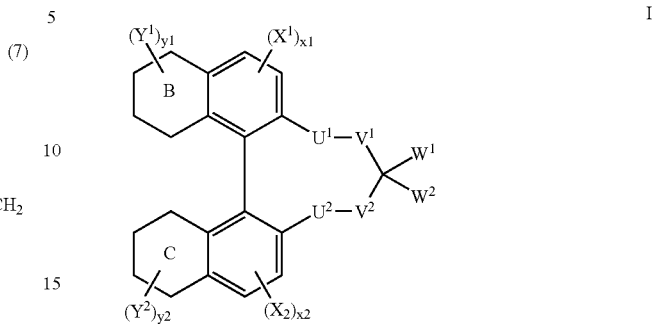

I wherein
$X^1, X^2, Y^1$ and $Y^2$ are independently of each other H; F; Cl; Br; I; CN; SCN; $SF_5$; straight chain or branched alkyl with 1 to 25 C atoms which may be unsubstituted, mono- or poly-substituted by F, Cl, Br, I or CN, one or more non-adjacent $CH_2$ groups optionally being replaced, in each case independently from one another, by —O—, —S—, —NH—, —$NR^0$—, —C(=O)—, —C(=O)O—, —OC(=O)—, —OC(=O)—O—, —S—C(=O)—, —C(=O)—S—, —CH=CH— or —C≡C— in such a manner that O and/or S atoms are not linked directly to one another; a polymerizable group; or cycloalkyl or aryl group with 1 to 20 C atoms that is optionally mono- or polysubstituted by L or by a polymerizable group,
$R^0$ is H or alkyl with 1 to 4 C atoms,
x1 and x2 are independently of each other 0, 1 or 2,
y1 and y2 are independently of each other 0, 1, 2, 3 or 4,
B and C are independently of each other an aromatic or partially or fully saturated aliphatic six-membered ring, wherein one or more CH groups are optionally replaced by N and one or more $CH_2$ groups are optionally replaced by O and/or S,
one of $W^1$ and $W^2$ is -$Z^1$-$A^1$-R, and the other is $R^1$, provided that $W^1$ and $W^2$ are not both H at the same time,
$U^1$ and $U^2$ are independently of each other $CH_2$, O, S, C(=O) or C(=S),
$V^1$ and $V^2$ are independently of each other $(CH_2)_n$,
n is an integer from 1 to 7,
$Z^1$ is —O—, —S—, —C(=O)—, —C(=O)—O—, —OC(=O)—, —O—C(=O)O—, —C(=O)—$NR^0$—,
—$NR^0$—C(=O)—, —$OCH_2$—, —$CH_2O$—, —$SCH_2$—, —$CH_2S$—, —$CF_2O$—, —$OCF_2$—, —$CF_2S$—, —$SCF_2$—, —$CH_2CH_2$—, —$CF_2CH_2$—, —$CH_2CF_2$—, —$CF_2CF_2$—, —CH=N—,
—N=CH—, —N=N—, —CH=CH—, —CF=CH—, —CH=CF—, —CF=CF—, —C≡C—, —CH=CH—C(=O)O—, —OC(=O)—CH=CH— or a single bond,
$A^1$ is a single bond,
R is: H; F; Cl; Br; I; CN; SCN; OH; $SF_5$; straight chain or branched alkyl with 1 to 25 C atoms which is unsubstituted, mono- or polysubstituted by F, Cl, Br, I or CN, one or more non-adjacent $CH_2$ groups optionally being replaced, in each case independently from one another, by —O—, —S—, —NH—, —$NR^0$—, —C(=O)—, —C(=O)O—, —OC(=O)—, —OC(=O)—O—, —S—C(=O)—, —C(=O)—S—, —CH=CH— or —C≡C— in such a manner that O and/or S atoms are not linked directly to one another, and R$^1$ is: H, F and straight chain alkyl with 1 to 12 C atoms wherein one or more H atoms may be replaced with F or CN, and one or more non-adjacent CH$_2$ groups are optionally replaced, in each case independently from one another, by —O—, —S—, —NH—, —N(CH$_3$)—, —CO—, —COO—, —OCO—, —OCO—O—, —S—CO—, —CO—S—, —CH═CH— or —C≡C—, in such a manner that oxygen atoms are not linked directly to one another.

2. A chiral compound according to claim 1, selected from those of the following formulae I-1

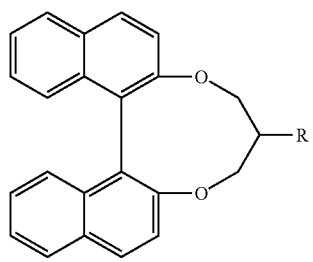

I-1 wherein R has the meaning given for formula I, provided that R is not H.

3. A chiral compound according to claim 1, comprising at least one photoisomerizable group.

4. A liquid crystal mixture comprising at least one chiral compound according to claim 1.

5. A polymerizable liquid crystal mixture comprising at least one compound of formula I according to claim 1 and at least one polymerizable mesogenic compound, which can be said compound of formula I or an additional polymerizable mesogenic compound.

6. A chiral linear or crosslinked liquid crystal polymer obtained by polymerizing a mixture according to claim 5.

7. A liquid crystal display which comprises a chiral compound according to claim 1.

8. A liquid crystal display of claim 7, which is a STN, TN, AMD-TN, temperature compensation, ferroelectric, guest-host, phase change, or surface-stabilized or polymer-stabilized cholesteric texture display.

9. An active or passive optical element, which comprises a chiral compound according to claim 1.

10. An active or passive optical element of claim 9, which is a polarizer, compensator, alignment layer, color filter or holographic element.

11. An adhesive composition, synthetic resin with anisotropic mechanical properties composition, cosmetic composition or pharmaceutical composition, which comprises a chiral compound according to claim 1.

12. A cholesteric liquid crystal mixture comprising a chiral component which contains at least one chiral compound according to claim 1, and further comprising a nematic component which contains one or more nematic or nematogenic compounds.

13. A cholesteric or SSCT display comprising a mixture according to claim 12.

14. A chiral compound of formula I of claim 1, wherein R$^1$ is H.

15. A chiral compound of formula I of claim 1, wherein Z$^1$ is a single bond.

16. A chiral compound of formula I of claim 1, wherein U$^1$ and U$^2$ are each O.

17. A chiral compound of formula I of claim 1, wherein n is 1.

18. A chiral compound of formula I of claim 1, wherein B and C are each benzene rings.

19. A chiral compound of formula I of claim 1, wherein y1 and y2 are each 0.

20. A chiral compound of formula I of claim 1, wherein x1 and x2 are each 0.

21. A chiral compound of formula I of claim 1, wherein R is OH, Cl, Br or I.

22. A chiral compound of claim 1, wherein each polymerizable group, if present, is of the formula P-Sp-X- wherein:

P is CH$_2$═CW$^1$—COO—,

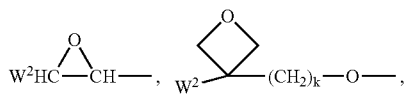

CH$_2$═CW$^2$—O—, CH$_3$—CH═CH—O—, HO—CW$^2$W$^3$—, HS—CW$^2$W$^3$—, HW$^2$N—, HO—CW$^2$W$^3$—NH—, CH$_2$═CW$^1$—CO—NH—, CH$_2$═CH—(COO)$_{k1}$-Phe-(O)$_{k2}$-, Phe-CH═CH—, HOOC—, OCN— or W$^4$W$^5$W$^6$Si, where W$^1$ is H, Cl, CN, phenyl or alkyl with 1 to 5 C-atoms, W$^2$ and W$^3$ are independently of each other H or alkyl with 1 to 5 C-atoms, W$^4$, W$^5$ and W$^6$ are independently of each other Cl, oxaalkyl or oxacarbonylalkyl with 1 to 5 C-atoms, Phe is 1,4-phenylene, and k1 and k2 are independently of each other 0 or 1;

Sp is a spacer group having 1 to 25 C atoms or a single bond;

X is —O—, —S—, —OCH$_2$—, —CH$_2$O—, —C(═O)—, —C(═O)O—, —OC(═O)—, —OC(═O)—O—, —C(═O)—NR$^0$—, —NR$^0$—C(═O)—, —OCH$_2$—, —CH$_2$O—, —SCH$_2$—, —CH$_2$S—, —CH═CH—C(═O)O—, —OC(═O)—CH═CH— or a single bond, where R$^0$ is H or alkyl with 1 to 4 C atoms.

23. A chiral compound of claim 3, wherein the photoisomerizable group is a group with a C═C, C═N or N═N double bond.

24. A chiral compound of claim 3, wherein one or both of W$^1$ and W$^2$ denote -Z$^1$-A$^1$-R— and Z$^1$ is a photoisomerizable group selected from —CH═CH—COO— or —OCO—CH═CH—.

* * * * *